United States Patent [19]

Campillo et al.

[11] 4,415,265

[45] Nov. 15, 1983

[54] METHOD AND APPARATUS FOR AEROSOL PARTICLE ABSORPTION SPECTROSCOPY

[75] Inventors: Anthony J. Campillo, Nesconset; Horn-Bond Lin, Manorville, both of N.Y.

[73] Assignee: The United States of America as represented by the U.S. Department of Energy, Washington, D.C.

[21] Appl. No.: 277,442

[22] Filed: Jun. 25, 1981

[51] Int. Cl.³ .............................................. G01N 21/39
[52] U.S. Cl. .................................... 356/338; 356/318; 356/342
[58] Field of Search ............... 356/317, 318, 338, 342; 250/524

[56] References Cited

U.S. PATENT DOCUMENTS 3,741,658  6/1973  Haclni et al. ......................... 356/346
3,811,778  5/1974  Hadeishi .
4,211,487  7/1980  Morrison et al. ................ 250/574 X

OTHER PUBLICATIONS

Whitby et al., "Atmospheric Aerosols-Characteristics and Measurement", date and source unknown.
Bright et al., "Measuring Aerosol Particles", *Chemical Technology*, vol. 9, No. 11, Nov. 1979.
Hu et al., "New Thermooptical Measurement Method and a Comparison With Other Methods", *Applied Optics*, vol. 12, No. 1, Jan. 1973.
Lin et al., "A Non-Destructive Detector ... ", *J. Chromatography*, vol. 206, p. 205, 1981.
Boccara et al., "Thermo-optical Spectroscopy ... ", *App. Phys. Lett.*, vol. 36, No. 2, Jan. 1980.
Fournier et al., "Sensitive *In Situ* Trace-Gas Detection ... ", *App. Phys. Lett.*, vol. 37, No. 6, Sep. 1980.
Melfi, "Remote Sensing for Air Quality Management", *Topics in Applied Physics*, vol. 14, Springer-Verlag, 1976.
Terhune et al., "Spectrophone Measurements ... ", *Optics Letters*, vol. 1, No. 2, Aug. 1977.
Bruce et al., "In-Situ Measurements ... ", *Applied Optics*, vol. 16, No. 7, Jul. 1977.

Primary Examiner—John K. Corbin
Assistant Examiner—Matthew W. Koren
Attorney, Agent, or Firm—Robert H. Whisker; Paul A. Gottlieb; Richard G. Besha

[57] ABSTRACT

A method and apparatus for determining the absorption spectra, and other properties, of aerosol particles. A heating beam source provides a beam of electromagnetic energy which is scanned through the region of the spectrum which is of interest. Particles exposed to the heating beam which have absorption bands within the band width of the heating beam absorb energy from the beam. The particles are also illuminated by light of a wave length such that the light is scattered by the particles. The absorption spectra of the particles can thus be determined from an analysis of the scattered light since the absorption of energy by the particles will affect the way the light is scattered. Preferably the heating beam is modulated to simplify the analysis of the scattered light. In one embodiment the heating beam is intensity modulated so that the scattered light will also be intensity modulated when the particles absorb energy. In another embodiment the heating beam passes through an interferometer and the scattered light reflects the Fourier Transform of the absorption spectra.

15 Claims, 4 Drawing Figures

METHOD AND APPARATUS FOR AEROSOL PARTICLE ABSORPTION SPECTROSCOPY

BACKGROUND OF THE INVENTION

The United States Government has rights in this invention pursuant to Contract Number DE-AC02-76CH00016, between the United States Department of Energy and Associated Universities, Inc.

This invention relates to the study of particles, whether liquid or solid, suspended in gas and, more particularly, to a method and apparatus for determining the electromagnetic radiation absorption spectra of such particles.

Such suspensions of particles, or aerosols, and their effects are important to many disciplines. In health problems of particulate inhalation, smoke detection and radiation transport via particles are of concern, Environmentalists are worried about smog formation, particulate effects on visibility, and particulate monitoring. Meterologists study fogs and haze and utilize cloud seeding techniques. And, of course, the industrial importance of various aerosols and sprays hardly needs to be emphasized. For these and other reasons the study of aerosols, and more particularly aerosol particles has become of increasing importance.

An important property of particles is the manner in which they absorb electromagnetic radiation. When the absorption is plotted as a function of absorbed radiation wavelength, the resulting pattern is called a spectrum. The spectrum may be used to deduce the chemical composition of the particles through characteristics identifying features peculiar to certain species. This in turn provides insight into the chemistry of aerosol formation. However, there are other instances where the absorption of electromagnetic radiation by particulate matter is of interest in its own right. For example, the role aerosols play in heating or cooling of the atmosphere is determined largely by scattering and absorption of electromagnetic radiation by the particles. This in turn may affect global or local climate. However, prior to the present invention, no techniques for directly determining such particle spectra, as opposed to the absorbtion spectra for an aerosol as a whole, are believed to have been known.

One technique which has proven useful in the study of aerosol particles has been the study of the intensity and angular distribution of light scattered by such particles. Techniques incorporating this approach have proven to be very sensitive, being capable of detecting single particles in the micron size range, and provide information about the size, shape, and index of refraction of particles. However, ordinary light scattering techniques provide little, if any, information about the absorbtion spectra of aerosol particles.

A technique which has provided certain amounts of information about the absorbtion spectra of gases and particles suspended in gases is known as "photoacoustic detection". Such devices utilize a tuneable source of electromagnetic energy, such as a $CO_2$ laser, which projects a beam of photons through a gas sample. As the laser is tuned through the absorption bands of the sample, energy is absorbed by the sample, causing an increase in pressure which then may be detected by a microphone. To improve the sensitivity of this technique, the beam may be "chopped" (i.e., on-off modulated) to provide a more easily detected signal. This technique has been used to make infrared absorption measurements, albeit at high concentration, on smokes and dusts. The sensitivity of this technique is, however, limited by the absorption of any background gases which may be present.

Another technique which has been used to make absorption measurements is known as "phase fluctuation optical heterodyne spectroscopy." In this technique, a first beam from a laser is divided by a beam splitter and one portion is passed through a gas sample containing particles. A second beam, which is sufficiently intense to cause localized heating of the sample, and which may be tuned through the region of the spectrum which is of interest is also passed through the sample. As the second beam is tuned through the absorption bands of the gas or of the particles contained in the gas, energy is absorbed by the sample, causing a change in the index of refraction of the gas, which in turn causes a difference in the phase relation between the two portions of the first beam. By measuring these phase changes the absorption spectrum may be deduced, however, in particle measurement applications this technique is also limited by the absorption of background gases.

Still another technique which is used to obtain absorption measurements is known as "differential absorption light radar" (or LIDAR). In this technique, beams from two tunable lasers are separated by a small, fixed frequency difference and are projected through the sample if interest. A certain amount of light from each beam will be backscattered and may be detected. As the beams are scanned through the absorption bands of the sample, the differences in the backscattered light at each frequency provide information about the absorption bands of the sample. Though in this technique light is generally backscattered by particles, again the absorption spectra obtained is dominated by the properties of the gas.

Finally, another technique used for obtaining information about absorption spectra is known as "thermolensing." In this technique, a visible light beam from a first source and a heating beam from a second source, such as $CO_2$ laser, are both projected through a sample. As the $CO_2$ laser is scanned through the absorption bands of the sample, energy is absorbed, creating regions having slightly different densities, which act as lenses deflecting the visible light beam. These deflections in the beam may then be detected to obtain information about the absorption spectra of the sample. When this technique is applied to aerosol measurements, the information obtained is again dominated by the properties of the gas. This technique also suffers from the disadvantage that the detector must be on the opposite side of the sample from the laser sources.

In view of the above, it is apparent there is a need for an apparatus and method for determining the absorption spectra of aerosol particulates, which is both sensitive and is not dominated by the absorption spectra of background gases.

Thus, it is an object of the subject invention to provide a method and apparatus which are capable of determining the absorption spectra of particles in the atmosphere which are capable of single particle sensitivity.

It is another object of the subject invention to provide a method and apparatus which are capable of determining the absorption spectra of particles in the atmosphere in the presence of background gases having similar absorption spectra.

It is another object of the present invention to provide, in one embodiment, a method and apparatus capable of obtaining absorption spectra information, while at the same time obtaining information on particle size and index of refraction.

It is still another object of the present invention to provide, in other embodiments, a method and apparatus for obtaining absorption spectra information which does not require the use of a laser.

Other objects and advantages of the subject invention will be readily apparent to those skilled in the art from the description set forth below.

SUMMARY OF THE INVENTION

The above objects are obtained and the disadvantages of known techniques described above are overcome by means of an apparatus comprising a first source providing a beam of light projecting through a preselected region. (By "light" herein is meant electromagnetic radiation of a wavelength suitable for scattering by aerosol particles and preferably visible light.) This source may be a laser, such as a helium-neon laser, where it is desired to obtain size and index of refraction information as well as absorption spectra information, but may also be a broad spectrum light source such as an incandescent light. A second source provides a heating beam projecting through the same preselected region, and means for detecting the light scattered from particles within that region are also provided. (By "heating beam" herein is meant either a broad beam of electromagnetic radiation, which encompasses the region of the spectrum of interest, or a narrower beam which may be tuned through that region and which is sufficiently intense to cause substantial heating of the particles.)

In operation, the two beams are projected through a source gas containing particles within the region. Light from the first source is scattered by these particles and detected. Particles having absorption bands within the spectrum of the heating beam from the second source will absorb energy from that beam, which will affect the scattering of light from these particles by one of a number of physical phenomenon. The presence of particles having absorption bands within the spectrum of the heating beam may then be detected by the observation of the correlation between the intensity of the scattered light and the intensity of the heating beam. In a preferred embodiment the heating beam may be intensity modulated so that a corresponding modulation of the scattered light may be observed.

Without wishing to be bound by any particular theory, it is noted that there are believed to be several mechanisms leading to the modulation of the scattered light, including:
1. photophoresis (i.e., movement of particles by a "radiometric force" caused by the differential heating of one side of the particle) out of the illuminating light beam from the first source;
2. macroscopic "thermolensing" due to both gas and particle absorption of the heating beam and subsequent distortion of the observed light scattering profile;
3. change in a scattering cross-section due to the creation of a localized, refracting, heated gas shell surrounding the particle; and,
4. photothermally induced physical changes (e.g., size and shape of the particles).

In general mechanisms 1, 3 and 4 are particle specific while mechanism 2, "thermolensing" depends upon both particle and gaseous absorption. Since most atmospheric aerosol particles are volatile the modulation of the scattered light will be dominated in such cases by mechanism 4, "photothermally induced changes." In addition, there are many nonvolatile species of aerosol particles that exist under conditions where mechanisms 1 and 3 will dominate. Thus, the present invention has the advantage that for many species of aerosol particles the particle absorbtion spectra may be determined even in the presence of strongly absorbing background gases. In these cases the invention is capable of determining the spectrum of a single particle.

Other objects and advantages of the subject invention will be readily apparent to those skilled in the art from examination of the drawings and consideration of the detailed description of the embodiments set forth below.

BRIEF DESCRIPTION OF THE DRAWINGS

FIG. 1a shows a schematic illustration of the infrared source used in another embodiment of the subject invention.

DETAILED DESCRIPTION OF PREFERRED EMBODIMENTS

Figure 1:
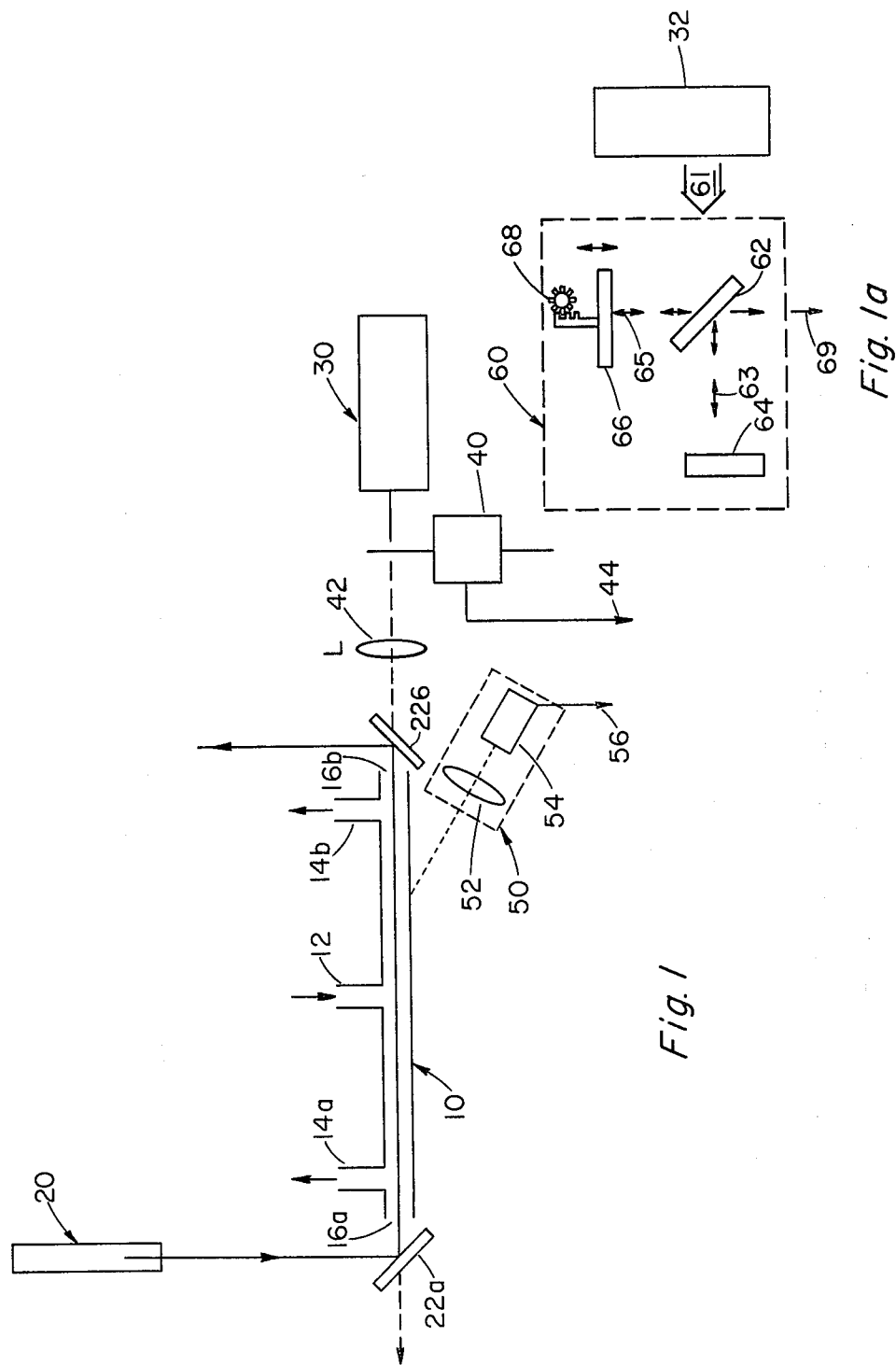
FIG. 1 shows a schematic illustration of one embodiment of the subject invention.

Turning now to FIG. 1, there is shown a first embodiment of the subject invention useful for measuring the absorption spectra of particles in a gas. In this embodiment, a transparent tube 10 having an inlet 12 and outlets 14a and 14b is provided. Inlet 12 is connected to a source, (not shown) which may be comprised of pumps or other apparatus well known to those skilled in the art, of an aerosol. The aerosol is drawn off through outlets 14a and 14b by vacuum means, (not shown) which again may be comprised of pumps or other means well known to those skilled in the art, so that a steady state concentration of sample gas is maintained in the tube 10.

Light source 20 projects a beam of visible light towards first mirror 22a where it is reflected so as to pass through tube 10 along the major axis to second mirror 22b, where it is again reflected.

In this embodiment, suitable for applications where it is desired to obtain information on the size and/or the index of refraction of the particles as well as absorption spectra information, light source 20 may comprise a laser, such as a helium-neon laser. In other embodiments light source 20 may comprise a simple incoherent light source such as an incandescent light.

Infrared source 30, which in this embodiment comprises a grating tunable infrared $CO_2$ laser, projects an infrared beam through modulator means 40. In the embodiment shown, modulator means 40 comprises a "chopper" disk with a plurality of aperatures through which the infrared beam may pass. The infrared beam may be 100% modulated at a selected frequency simply by rotating the disk at the appropriate rate. Of course, other means, particularly electro-optic means, for modulation of the infrared beam will be readily apparent to those skilled in the art.

The infrared beam then passes through lens 42 (preferably formed of Barium Fluoride) where it is more narrowly focussed and through second mirror 22b. Since mirrors 22a and 22b are formed from material, such as germanium, which is transparent to infrared radiation while highly reflective to visible light, the infrared beam passes down the major axis of tube 10 antiparallel to the light beam without any problems arising from one laser directly illuminating the other.

If particles are present in the gas flowing through tube 10 the light from source 20 will be scattered and detected by detector means 50. If the scattering particles have absorption bands within the spectrum of infrared source 30, the scattered light will have a modulation corresponding to the modulation of the infrared beam. If the scattering particles do not have absorption bands within the spectrum of the infrared beam, the scattered light will not be modulated or will have only a very slight modulation. By scanning through the infrared spectrum with the source 30 and detecting the presence or absence and extent of modulation with detector 50 the infrared absorption spectra of the particles in the gas sample may be obtained in situ.

In the embodiment shown, detector means 50 comprises a lens 52 and a photomultiplier 54. Other detector means would be obvious to those skilled in the art and the particular detector means chosen is not crucial to the present invention. The output 56 of photomultiplier 54 may be connected to instruments for recording or analysis. A reference signal 44 may be obtained from modulator 40 to aid in the synchronous detection of the presence of modulation in the output 56.

Turning now to FIG. 1a, there is shown an alternative infrared source and modulation means which may be used in place of infrared source 30 and modulation means 40 to form a second embodiment of the subject invention.

Second infrared source 32 comprises a broad spectrum source, such as a glowbar, which radiates substantially uniformly through the infrared. This broad spectrum infrared radiation passes through an interferometer 60. Interferometer 60 comprises a beam splitter 62, a fixed mirror 64 and a movable mirror 66. Beam splitter 62 is formed of a material such as Barium Fluoride and will typically transmit part 63 of incident beam 61 to fixed mirror 64 and reflect part 65 of beam 61 to movable mirror 66. (Normally the ratio of beam 63 to beam 65 will be 1:1 but slight variations from this ratio are not critical). Mirrors 64 and 66 are formed of materials such as silver, gold or aluminum and are highly reflective in the infrared and will reflect beam 63 and 65 back to beam splitter 62 where they recombine to form output beam 69.

When mirror 66 is moved by means of mechanism 68, the beam path length between mirrors 64 and 66 changes and different interference patterns are formed in output beam 68. As a result interferometer 60 allows only certain bands of infrared radiation to pass through tube 10, depending on the beam path length between mirrors 64 and 66.

If the beam path length is changed uniformly, there will again be a modulation of the scattered light as described above with respect to the first embodiment. However, in this embodiment the output 56 of photomultiplier 54 will represent the Fourier transform of the absorption spectrum of the particles. The actual absorption spectrum may be obtained by numerically determining the inverse Fourier transform function of the output 56 by means of computer techniques well known to those skilled in the art.

This embodiment has an advantage in that it allows a lower intensity broad band source to be used rather than very narrow band tunable lasers such as a $CO_2$ laser, which in general are restricted in the range over which they may be tuned.

It is important to note that in both of the above described embodiments if detector means 50 is positioned to observe light scattered at an angle of from about 5° to about 175°, the scattered light very quickly passes out of the infrared beam. Thus, there is very little chance for the kind of detrimental background gas effects that were noted with other types of apparatus, to effect the scattered beam.

It should be noted that currently available glowbar sources are somewhat limited in intensity so that embodiments using glowbar sources might be limited to the study of relatively large particles which would have sufficient cross-section to absorb substantial energy. However, if more intense broad band sources are developed or sources such as synchrotron radiation sources are used this embodiment would be useful over the full range of aerosol particle sizes.

Figure 2:
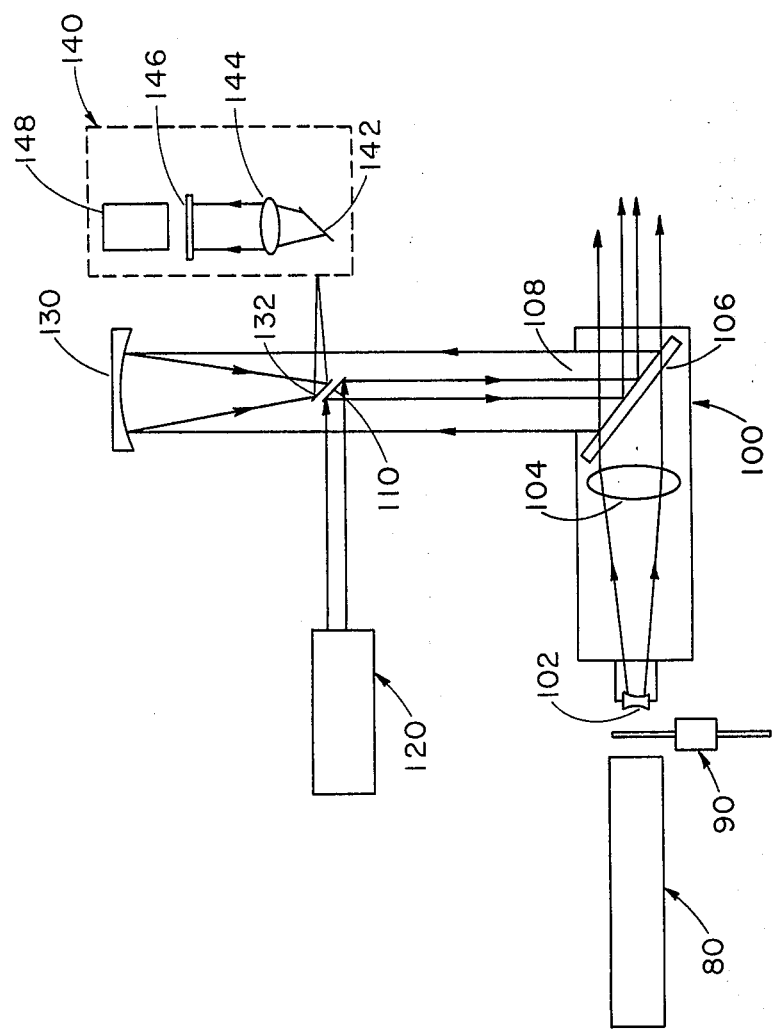
FIG. 2 shows a schematic illustration of another embodiment of the subject invention useful for remote, or field measurements of absorption spectra.

Turning now to FIG. 2, there is shown a third embodiment of the subject invention suitable for long range measurements of absorption spectra.

An infrared beam source 80 which may be a tunable $CO_2$ laser, projects a beam through modulator means 90, which may be a mechanical "chopper" as described above, and through telescope 100. Telescope 100 is comprised of lenses 102 and 104 and mirror 106, which is formed of a material such as germanium transparent to infrared radiation. Telescope 100 thus provides a collimated or focussed beam capable of projection over long distances.

Light source 120 comprises a pulsed visible laser, such as a frequency doubled Neodymium:YAG laser, which projects a tight coherent beam of light off of mirrors 110 and 106, so that the light beam is projected parallel with the infrared beam.

Backscattered light (i.e., light scattered at an angle of essentially 180°) is collected by telescope 100 and reflected from mirror 106 to focussing mirror 130, to mirror 132, and to detector 140. Detector 140 comprises mirror 142, lens 144, filter 146, and photomultiplier 148, which provides an output proportional to the intensity of the backscattered light. Filter 146 filters out background light, allowing only backscattered light from source 120 to reach photomultiplier 148.

Since light source 120 is pulsed, the output of detector 140 may be compared to a reference signal used to control the pulsing of source 120 in order to obtain distance information, in the manner commonly referred to as LIDAR (light radar). Further, as $CO_2$ laser 80 is scanned through the infrared spectrum, the output of detector 140 will also contain modulations which may be used to obtain absorption spectra information.

Those skilled in the art will note that this third embodiment to the subject invention bears some similarity to the differential absorption spectroscopy technique described in the Background Of The Invention section above. Further, since the backscattered light travels antiparallel to the infrared beam, it is subject to the effects of background gas absorption as described above. However, the subject invention in this embodiment retains at least two major advantages for remote measurement of absorption spectra. First, it is not necessary to provide two lasers which scan in unison with a small fixed frequency difference between lasers. This greatly simplifies construction of the sources. Second, and perhaps more important, the subject invention in this embodiment allows the remote measurement of absorption spectra in the infrared region, which was not possible before, since infrared radiation wavelengths are too long for good scattering measurements.

EXPERIMENTAL EXAMPLE

Experiments were conducted with an apparatus substantially as shown in FIG. 1. Submicron aerosol particles, generally in a polydisperse log normal size distribution with 0.3 micrometer geometric mean diameter and a geometric mean standard deviation of 2 were generated from an aqueous ammonium sulfate solution using a constant output atomizer and introduced at a constant rate into inlet 12 of tube 10. Tube 10 was approximately 20 centimeters long and had a 4 millimeter I.D. Vacuum connections were attached to outlets 14a and 14b to balance the flow into and out of tube 10 and to bypass open ends 16a and 16b. Linearly polarized light (633 nanometers) emitted by a helium-neon laser was directed through tube 10 along the major axis and elastically scattered off the particles. The horizontally polarized component was detected at an angle of 20° with respect to the forward transmitted beam using a photomultiplier.

A grating tunable $CO_2$ laser beam was superimposed spacially on the helium-neon beam in tube 10 and used to modify the visible scattered light. Depending on experimental conditions, modulation amplitudes as high as 40 percent were observed in the scattered light. At this level, the visible effect was quite striking when the infrared beam was modulated at a sub-Herz rate.

Although the modulation amplitude was observed to be linearly proportional to the $CO_2$ laser intensity, the intensity of the $CO_2$ laser was typically constrained to keep the modulation amplitude on the order of 1 percent or less to insure linear absorption measurements. In these instances a lock-in amplifier was employed to synchronously detect the ac component of the scattered light using a reference signal from modulator means 40 and the signal was displayed using a chart recorder.

Since it may be shown that for chemically identical polydisperse sized aerosols the modulation amplitude is linearly proportional to the particle absorption of the infrared radiation, a plot of the modulation amplitude vs. the $CO_2$ laser wavelength for an arbitrary aerosol will yield a true relative absorption spectrum of the particles. This occurs because the infrared absorption cross-section per unit mass is independent of particle size. Thus, this apparatus and technique are appropriate to application requiring the determination of the relative composition of particles; for example, the ratio of $(NH_4)^+$ to $(SO_4)^{--}$ ions. In this latter example the $(NH_4)^+$ ion would be excited by a 3.39 micrometer wavelength, while the $(SO_4)^{--}$ ion would preferentially absorb 9.2 micrometer $CO_2$ laser radiation.

In one experiment using the methods described above, measurements were made on ammonium sulfate particles to determine the 920 to 1080 $cm^{-1}$ absorption spectrum.

The detected modulation of scattered light showed a strong $(SO_4)^{--}$ ion band at 1110 $cm^{-1}$ and a weak particulate water background. This was in agreement with the known properties of ammonium sulfate.

This good agreement demonstrates that the photothermal scattering technique yields a valid particle relative absorption spectrum.

Figure 3:
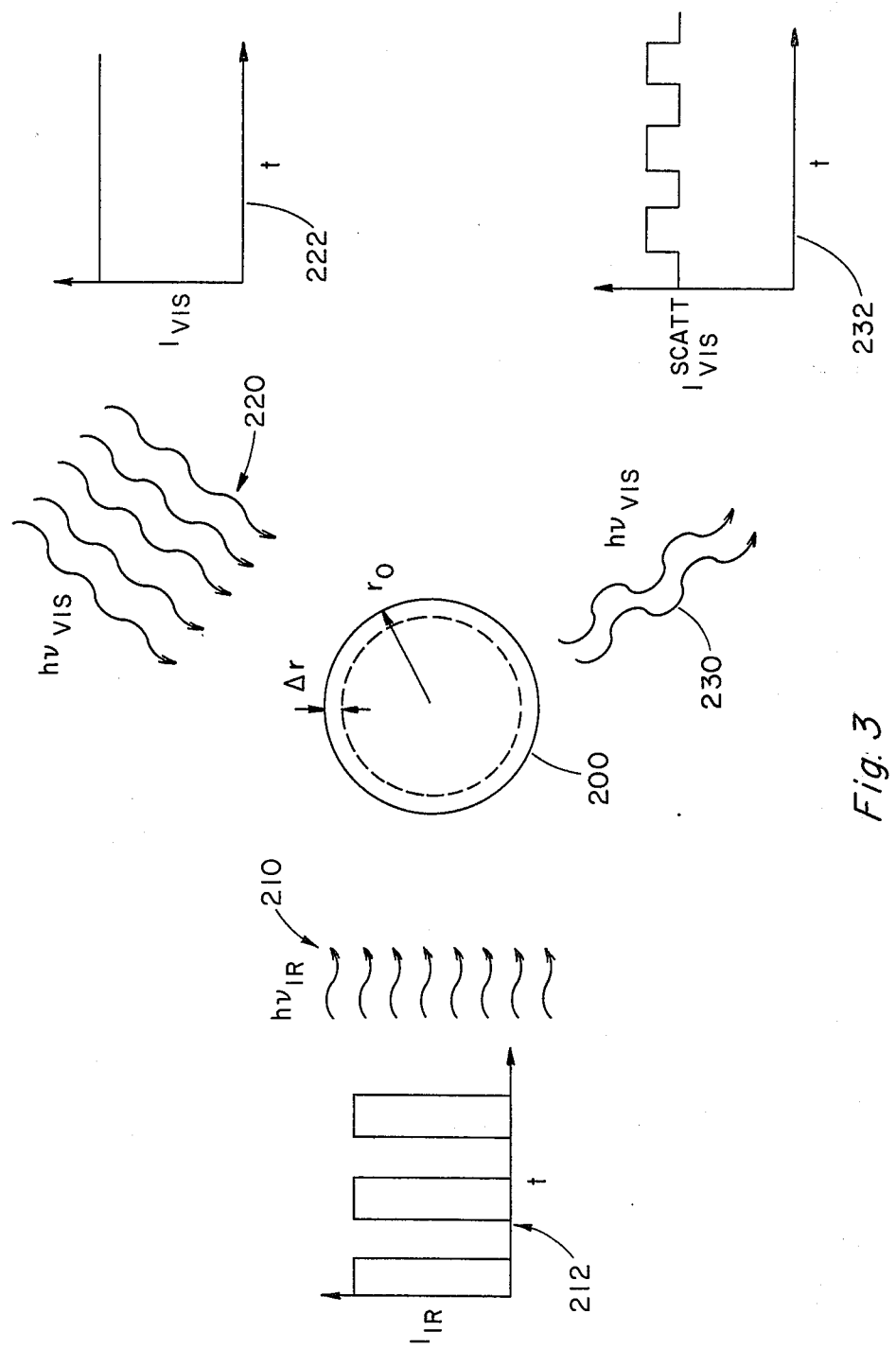
FIG. 3 is a schematic representation of the modulation of the visible light beam by the infrared beam as mediated by a particle.

In order to more clearly explain the operation of the subject invention, and without wishing to be bound by any particular theory of operation, reference is made to FIG. 3, which schematically shows the interaction between the visible radiation and the infrared radiation upon which the subject invention relies.

A particle 200, schematically shown as having an ideal spherical shape, is irradiated by infrared radiation 210. Infrared radiation 210 is modulated as is shown in the graph of $I_{ir}$ vs. t 212. During the on periods shown in graph 212, particle 200 will be reduced from its nominal radius $r_0$ by an amount delta r. During the off periods shown in graph 212, the particle will recondense to its nominal radius $r_0$, provided sufficient time is allowed. For ammonium sulfate particles frequencies up to approxiamtely 500 Hertz with about a 50% duty cycle have been used successfully. This implies that a particle will evaporate and recondense in a time period of less than about 1 millisecond.

The particle is also illuminated by constant amplitude light 220 as shown in graph 222. This light is elastically scattered by particle 200, producing scattered light 230, which may then be detected. The physical changes produced in particle 200 by infrared radiation 210 modulate the light 230, as is shown in graph 232. Thus, the presence of modulation in scattered light 230 implies that particle 200 has absorption bands within the spectrum of infrared radiation 210.

The above descriptions of preferred embodiments of the subject invention and the examples given are given by way of illustration only. The limitations on the subject invention are to be found only in the claims set forth below.

We claim:
1. An absorption spectrometer apparatus comprising:
    (a) a source providing a beam of light, said beam passing through a preselected region,
    (b) a source providing a variable wavelength heating beam, said heating beam also passing through said region and said heating beam having a known spectrum,
    (c) means for modulating said heating beam; and,
    (d) means for detecting the intensity of light scattered from particles within said region, whereby the presence of particles having absorption bands within the spectrum of said heating beam may be detected by observation of the intensity of said scattered light.
2. An apparatus as described in claim 1, wherein said modulating means comprises an interferometer and said heating beam source comprises a broad spectrum infrared source.
3. An apparatus as described in claim 1, wherein said heating beam source comprises a tunable narrow band laser, and said modulating means is an intensity modulating means.
4. An apparatus as described in claims 1, 2, or 3, wherein said light source comprises a laser.
5. A method for detecting the presence of particles having particular absorption bands comprising the steps of:

(a) illuminating said particles with light;
(b) further illuminating said particles with an intensity modulated and wavelength variable heating beam, the spectrum of said heating beam including said particular bands; and
(c) detecting light scattered by said particles, whereby the presence of said particles may be detected by observation of the intensity of said scattered light.

6. A method as described in claim 5, wherein said heating beam is modulated by passing a broad spectrum beam through an interferometer and further, wherein the modulation of said scattered light corresponds to the Fourier transform of the absorption spectrum of said particles.

7. A method as described in claim 9, wherein said heating beam is produced by a tunable laser.

8. A method as described in claims 5, 6, or 7, wherein said scattered light is detected at an angle of from about 5° to about 175° with respect to the forward direction of said light beam.

9. A method as described in claims 5, or 7, wherein said scattered light is backscattered light.

10. An apparatus comprising:
(a) a first source providing a beam of light, said beam passing through a preselected region,
(b) a second source providing a heating beam, said heating beam passing through said region in parallel with the first source and said heating beam having a known spectrum; and,
(c) means for detecting the intensity of backscattered light from particles within said region, whereby the presence of particles having absorption bands within the spectrum of said heating beam may be detected by observation of the correlation between the intensity of said scattered light and the intensity of said heating beam.

11. An apparatus as described in claim 10, wherein said beams are projected and said backscattered light is collected through a telescope.

12. An apparatus as described in claim 10, further comprising means for modulating said heating beam.

13. An apparatus as described in claim 12, wherein said heating beam source comprises a tunable narrow band laser, and said modulating means is an intensity modulating means.

14. Apparatus as described in claims 12 or 13, wherein said detecting means is positioned to detect light scattered at an angle of from about 5° to 175°, with respect to the forward direction of said light beam.

15. A method of determining the absorption spectrum of aerosol particles comprising the steps of:
(a) illuminating said particles with a beam of light;
(b) heating said particles with a wavelength tunable heating beam;
(c) scanning the wavelength of the heating beam through the absorption band of the particles; and
(d) detecting the intensity of visible light scattered by said particles as a function of heating beam wavelength whereby the absorption spectrum of the particles may be determined.

* * * * *